United States Patent
Redding, Jr. et al.

[11] Patent Number: 6,110,501
[45] Date of Patent: Aug. 29, 2000

[54] SEEDED MICROCAPSULES FOR USE IN TABLETS, PHARMACEUTICAL AGENTS AND NUTRITIONAL COMPOUNDS

[75] Inventors: Bruce K. Redding, Jr.; Jerome Harden, both of Philadelphia, Pa.

[73] Assignee: Verion Inc., Exton, Pa.

[21] Appl. No.: 09/226,356

[22] Filed: Jan. 6, 1999

Related U.S. Application Data

[63] Continuation of application No. 09/111,897, Jul. 8, 1998, which is a continuation-in-part of application No. 08/908,232, Aug. 7, 1997, abandoned, which is a continuation of application No. 08/576,636, Dec. 21, 1995, abandoned, which is a continuation of application No. 08/137,439, Nov. 8, 1993, abandoned.
[60] Provisional application No. 60/082,165, Apr. 17, 1998.

[51] Int. Cl.[7] ............................. A61K 9/50; A61K 9/51
[52] U.S. Cl. ................... 424/490; 424/491; 424/492; 424/493; 424/494; 424/495; 424/496; 424/497; 424/498
[58] Field of Search ........................ 424/498, 499, 424/500, 501, 502, 490, 464, 465, 489, 491, 492, 493, 494, 495, 496, 497, 451, 452, 463

[56] References Cited

U.S. PATENT DOCUMENTS

| | | | |
|---|---|---|---|
| 2,978,331 | 4/1961 | Ferrari | 99/91 |
| 2,978,332 | 4/1961 | Ferrari | 426/99 |
| 3,959,496 | 5/1976 | Jackel et al. | 426/25 |
| 4,842,863 | 6/1989 | Nishimura et al. | 424/438 |
| 5,098,725 | 3/1992 | Rotman et al. | 426/98 |
| 5,178,878 | 1/1993 | Wehling et al. | 424/466 |
| 5,178,894 | 1/1993 | Rudel | 426/549 |
| 5,418,010 | 5/1995 | Janda et al. | 427/213.31 |
| 5,639,475 | 6/1997 | Bettman et al. | 424/466 |
| 5,709,886 | 1/1998 | Bettman et al. | 424/495 |
| 5,941,256 | 8/1999 | Guay et al. | 132/321 |

FOREIGN PATENT DOCUMENTS

| | | | |
|---|---|---|---|
| 0 411 326 | 2/1991 | European Pat. Off. | A23L 1/05 |
| 96/22676 | 8/1996 | WIPO | A01D 2/02 |
| 98/07324 | 2/1998 | WIPO | A21D 2/02 |

*Primary Examiner*—James M. Spear
*Attorney, Agent, or Firm*—Synnestvedt & Lechner LLP

[57] ABSTRACT

A microcapsule having a core, a shell and seeds fully or partially embedded in said shell. The core and seeds are active substances which preferably function as a leavening agent. The shell is composed of either a water soluble or meltable natural polymer, including vegetable waxes. When the shell is ruptured, the active substances will react with each other and the dough mixture thereby producing a leavening effect and/or dough conditioning effect in baked goods.

14 Claims, 5 Drawing Sheets

FIG. 7A
WET GRANULATION

FIG. 7B
DRY GRANULATION

FIG. 7C
DIRECT COMPRESSION

SEEDED MICROCAPSULES FOR USE IN TABLETS, PHARMACEUTICAL AGENTS AND NUTRITIONAL COMPOUNDS

CONTINUING DATA

This application is a continuation of application Ser. No. 09/111,897 Filed Jul. 8, 1998, Provisional patent application No. 60/082,165 filed Apr. 17, 1998, and is a Continuation-In-Part of U.S. patent application Ser. No. 08/908,232 filed Aug. 7, 1997 now abandoned which is a continuation of U.S. patent application Ser. No. 08/576,636, filed Dec. 21, 1995, now abandoned, which is a continuation of U.S. patent application Ser. No. 08/137,439, filed Nov. 8, 1993, now abandoned.

FIELD OF THE INVENTION

This invention relates generally to encapsulated materials and, more specifically, to microcapsules for use in manufacturing tablets for use as an active pharmaceutical agent and/or as a nutritional compound.

BACKGROUND OF THE INVENTION

Encapsulation is widely used in the pharmaceutical and nutritional industries. In these industries, encapsulation is primarily used for taste masking and as a buffering agent. In general, encapsulation is used to protect an inner core made from one substance (usually an active or a desired substance) with an outer shell made from a different substance (usually an excipient or filler). The core material would normally be subject to the degradation effects of acid (e.g., in the stomach), oxygen, heat, moisture, etc. However, while encapsulated, the degradation of the core material is greatly reduced if not completely prevented. This greatly increases the shelf-life of the core material.

A common technique for encapsulating medicines is spray drying. Spray drying is relatively inexpensive and produces a finely divided product that is readily used in the preparation of finished pharmaceutical agents. However, spray drying is very limited in its applications and is usually utilized with relatively large core materials.

In view of their relatively long shelf life, high durability, and relatively low cost, tablets are a favorite means of delivering a medicine or nutritional supplement.

Normally, there is only one machine that can make a tablet, namely a tablet punch. If the medicine or nutritional supplement is not directly compressible, it must be made so by using wet granulattion or dry granulation. Medicinal tablets are usually formed by direct compression of an active ingredient. However, if the active ingredient is not compressible, other ingredients (e.g., excipients or fillers) may be used or other techniques must be employed to form a solid dosage form. Unfortunately, each of the aforementioned methods has its drawbacks.

In direct compression, a powdered pharmaceutical is mixed with water and the mixture is compressed to form a tablet. Wet and dry granulation use powdered excipients in their formulations to make tablets. Unfortunately, when encapsulated pharmaceuticals (having dimensions on the order of the powder) are utilized, a relatively high percentage of the microcapsules are destroyed or defaced by the high pressure applied to same or by abrasive components present in the excipient.

Similar problems are encountered when microcapsules are incorporated in a compressed powder matrix (including animal feed pellets, compressed vitamin and mineral formulations) and pharmaceutical tablets (i.e., pills) for both human and veterinary applications.

It is desirable to have a method of encapsulation that can withstand the pressure of manufacturing tablets and reduce the amount of waste created by tablet manufacturing process. Also, it is desirable to have a tablet that can release medicine in a more controlled process and with more precise timing.

SUMMARY OF THE INVENTION

The subject invention relates to a tablet having microencapsulated compounds and a process for manufacturing said tablets. Since pressure is used in a tablet press or pelletizing operation, an important concern is to prevent the microcapsules from breaking under such pressure. The shell of the microcapsules must protect the core material during the manufacturing of the tablet or pelletizing operation and not break until a desired or triggering event (e.g., time, temperature, moisture, etc.) occurs. If the shell of the microcapsule ruptures during the tablet pressing the core material will be prematurely released.

One method of preventing this premature rupturing of the shell is by mining the shell with "seeds". The "seeds" of such microcapsules are selected to increase the physical strength of the shell; they may also be chosen to enhance or exploit a specific chemical and/or physical reaction through a controlled or predictable release of said capsule. Seeded microcapsules, when used as a means to deliver a medicinal agent, ultimately produce a more useful and higher quality end-product.

The seeding agents may be completely embedded within the shell material, they may protrude partially through the shell's surface, or they may consist of a combination of embedded and protruding seeds. In addition to enhancing the end-product, the seed can give the shell different strength, stability, weight, balance, buoyancy, or dissolution characteristics. By adjusting the size of the seed or the thickness of the shell layer, the seeds can either be completely immersed in the shell or a portion of the seeds can protrude through the shell.

The subject invention is directed to providing a tablet that utilizes microcapsules wherein an active substance forms the core of the microcapsule and other chemical agents (referred to as seeds) are dispersed throughout the microcapsule shell to strengthen the shell. In another embodiment, the chemical agents can be chosen for their reactance with the various environments encountered by a tablet (e.g., saliva, stomach acid, gastral and intestinal fluids, etc.).

The above and other features and advantages of the present invention will be apparent from a reading of the following detailed description in conjunction with the accompanying drawings.

DETAILED DESCRIPTION OF THE PREFERRED EMBODIMENT

In describing a preferred embodiment of the invention, specific terminology has been selected for the sake of clarity. However, the invention is not intended to be limited to specific terms so selected, and it is to be understood that each specific term includes all technical equivalents that operate in a similar manner to accomplish a similar purpose.

Preferred embodiments of the present invention will now be described in detail with reference to the accompanying drawings in which a single seeded microcapsule is generally indicated at 10. As used herein, a seeded microcapsule is a microcapsule having an active core 12 surrounded by a shell 14 and seeding agents 16 disposed in the shell 14. Usually, a microcapsule has a maximum diameter less than one millimeter. Seeding agents 16 are typically in the form of particulate matter but may also be comprised of liquids, solids or gases which are themselves encapsulated by a shell.

Figure 1:
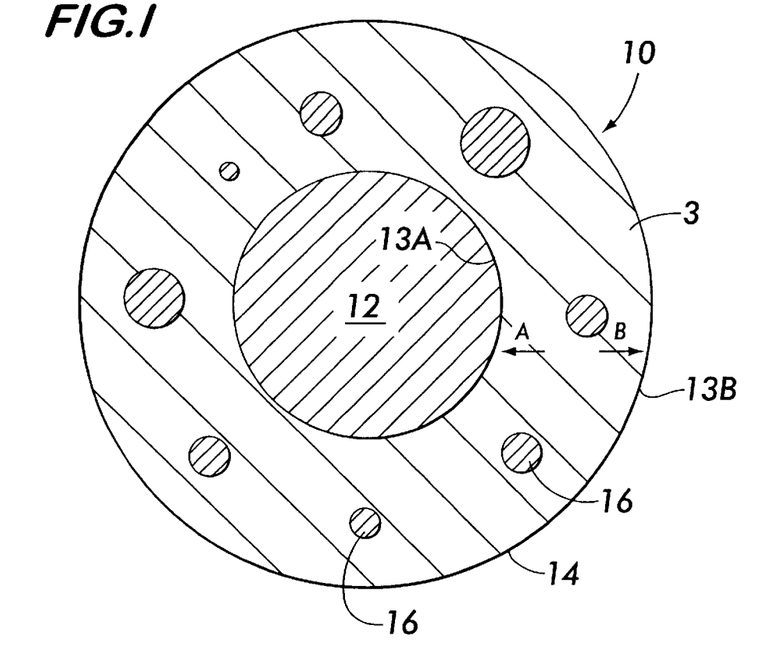
FIG. 1 is a cut-away view of a seeded microcapsule in accordance with the present invention.

FIG. 1 is a cut-away view of a typical seeded microcapsule 10 having a core 12 and a shell 14. A plurality of seeds 16 are shown randomly dispersed and completely embedded within the shell 14.

The shell 14 includes an inner surface 13A and an outer surface 13B. The shell thickness is the radial distance between the inner surface 13A and the outer surface 13B. By adjusting the particle size of the seeds 16 or the thickness A of the shell 14, the seed can be totally embedded in the shell 14 (i.e., each seed is completely between the inner and outer shell surfaces 13A, 13B).

Figure 2:
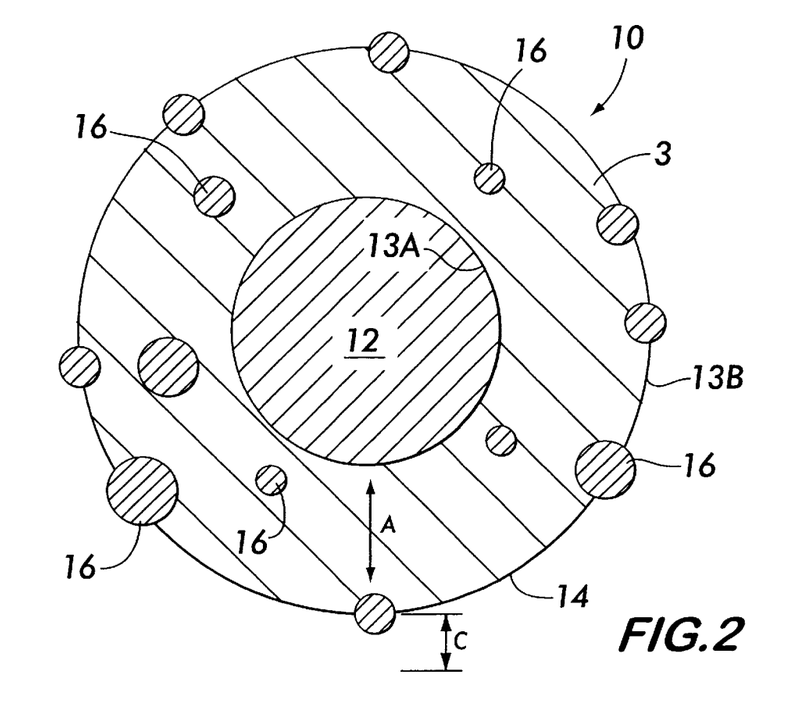
FIG. 2 is a seeded microcapsule in accordance with the present invention in which the seeds are partially embedded and partially protrude through the surface of the shell.

Referring now to FIG. 2, an alternate embodiment of the invention is illustrated. In this embodiment, some of the plurality of seeds 16 protrude through the outer shell surface layer 13B. As opposed to the first embodiment illustrated in FIG. 1 in which the seed is totally protected from interaction with any other substance outside of the microcapsule, this embodiment allows at least a portion of the seeds to interact with its outside environment.

Normally, protruding seeds are used when the tablet is subjected to a higher compression stage during manufacturing.

Once again, by adjusting the particle size of the seeds 16, or the thickness of the shell 14, a portion, if not a majority, of the seeds are allowed to extend through the outer shell layer 13B.

As illustrated in FIG. 2, the average length of the exposed particulate is indicated by the letter C. The exposed particulate length C is dependant upon both the particle size of the seeds 16 in relation to the shell thickness, and upon the positioning of the seeds 16 within the shell layer.

In both of the aforementioned embodiments, the seeds 16 are placed in the shell to impart structural and functional characteristics to the microcapsule. The seeds 16 may also be chosen to achieve unique or specific release characteristics. The seeds 16 act to increase the structural integrity of the shell 15 by increasing the shell's resistance against sheer, pressure and abrasion. The seeds 16 may also enhance thermostability to a given material by changing the melting point of the shell or otherwise altering the thermal characteristics of the shell-seed combination. Another use of the seeds 16 is to alter the weight and/or balance characteristics of the resulting tablet. The seeds 16 may also be used to affect the solubility rate of an otherwise normal shell, thus acting as a basis for controlling or influencing the release of the core material.

Figure 3:
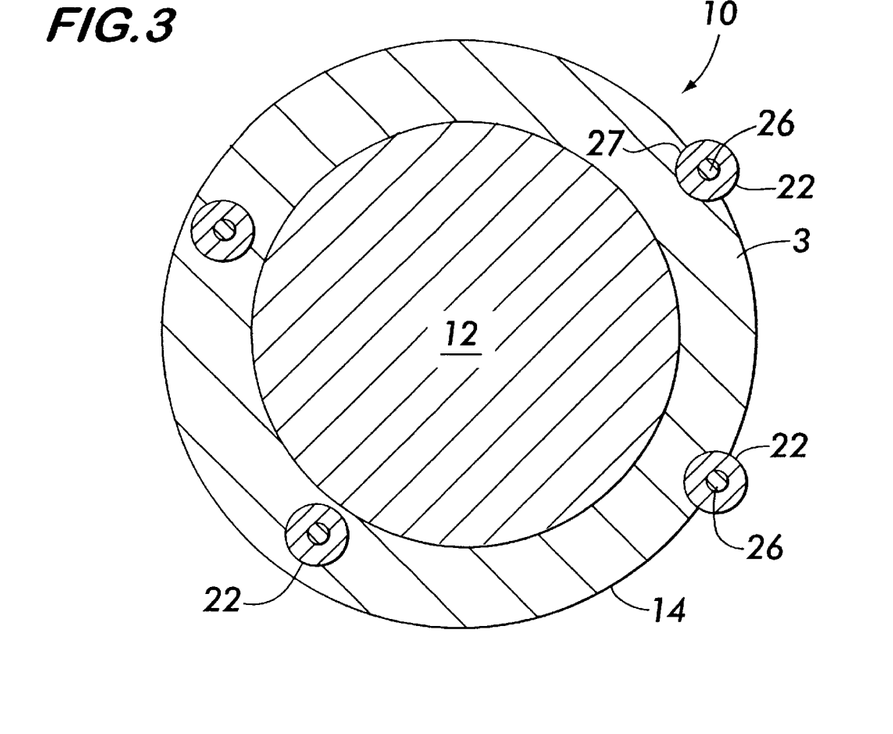
FIG. 3 is a cut-away view of a seeded microcapsule in which the seeds themselves are also encapsulated.

Referring now to FIG. 3, a third embodiment would involve the use of a relatively smaller encapsulated seed agents 22 wherein the seed compound 26 itself is encapsulated by a shell material 27 and together the encapsulated seed 22 is used as a seed within the primary shell 14 as either an embedded seed or a protruding seed.

In the above embodiments of the microcapsules, the shell can be composed of a variety of materials depending upon the application, and the desired physical strength and release characteristics. In the preferred embodiment, the material for the shell can be divided into five broad categories; namely, natural polymers, vegetable derived fats and waxes, animal waxes, synthetic polymers, and elastomers. Samples of each of the five broad categories follows.

| NATURAL POLYMERS | |
|---|---|
| CARBOXYMETHYLCELLULOSE | ZEIN |
| CELLULOSE ACETATE PHTHALATE | NITROCELLULOSE |
| ETHYLCELLULOSE | PROPYLHYDROXY-CELLULOSE |
| GELATIN | SHELLAC |
| GUM ARABIC | SUCCINYLATED GELATIN |
| STARCH | WAXES, PARAFFIN |
| BARK | PROTEINS |
| METHYCELLULOSE | DRAFT LIGNIN |
| ARABINOGALACTAN | NATURAL RUBBER |

| VEGETABLE DERIVED FATS AND WAXES | | |
|---|---|---|
| SOYBEAN | TRI-GLYCERIDES | MONO-DIGLYCERIDES |
| COTTONSEED | DI-GLYCERIDES | FATTY ACIDS |
| HYDROGENATED VEGETABLE OIL | | LAURIC ACID |
| PALMITIC OIL WAXES | | |

| ANIMAL DERIVED FATS AND WAXES | |
|---|---|
| ANIMAL TALLOW | BEEF FAT |

| SYNTHETIC POLYMERS | |
|---|---|
| POLYVINYL ALCOHOL | POLYVINYL CHLORIDE |
| POLYETHYLENE | POLYVINYLIDENE CHLORIDE |
| POLYPROPYLENE | CHLORINATED POLYETHYLENE |
| POLYSTYRENE | POLYACRYLONITRILE |
| POLYESTER | ACETYL COPOLYMER |
| POLYUREA | POLYURETHANE |
| EPOXY | POLYVINYLPYRROLIDONE |
| ETHYLENE VINYL ACETATE | POLYMETHYL |

| SYNTHETIC POLYMERS | |
| --- | --- |
| COPOLYMER | METHACYLATE |
| POLYVINYL ACETATE | POLYACRYLAMIDE |
| POLYHYDROXYETHYL METHACRYLATE | POLY(P-XYLYENE) |
| POLYETHER | |

| SYNTHETIC ELASTOMERS | |
| --- | --- |
| POLYBUTADIENE | ACRYLONITRILE |
| POLYISOPRENE | NITRILE |
| NEOPRENE | BUTYL RUBBER |
| CHLOROPRENE | POLYSILOXANE |
| STYRENE-BUTADIENE | HYDRIN RUBBER |
| ILICONE | ETHYLENE POLYMERS |

The above list is not meant to be exhaustive and other materials could be utilized as alternative shell materials. For use in medicinal or pharmaceutical tablets, only FDA approved shell coating materials should be used, and preferably only those chosen from the natural polymer, vegetable derived fats and waxes, or animal derived fats and waxes categories.

The core of a microcapsule can be composed of virtually any material depending on the ultimate use of the microcapsule. Generally, the core of the capsule can be composed of several materials falling into the following general categories:

A) Active pharmaceutical substances for human use
B) Active pharmaceutical substances for veterinary use
C) Active nutritional substances, including vitamins and minerals Examples of common active substances (for use in the core) include but are not limited to:

1. Aspirin
2. Acetaminophen
3. Ibuprofen
4. Ascorbic acid
5. Choline
6. Any over the counter pharmaceutical for human or veterinary applications approved by the U.S. Food and Drug Administration or such similar regulatory authority of any other nation.
7. Any prescription pharmaceutical for human or veterinary applications approved by the U.S. Food and Drug Administration or such similar regulatory authority of any other nation.
8. Any nutritional compound for human or veterinary applications approved by the U.S. Food and Drug Administration or such similar regulatory authority of any other nation.

In the above capsule constructions, the seeds of the capsule can be composed of several materials falling into the following general categories:

1. Any single or combination of pharmaceutical excipients for human or veterinary applications approved by the U.S. Food and Drug Administration (FDA) or such similar regulatory authority of any other nation.
2. Seeds which will react with the core material producing a desired or controlled effect.

Including, but not limited to the following:

| | | |
| --- | --- | --- |
| Acacia | Chlorobutanol | Lecithin |
| Alcohol | Cholesterol | Magnesium Aluminium |
| Alginic Acid | Citric Acid | Silicate |
| Ascorbic Acid | Pharmaceutical Coloring | Magnesium Carbonate |
| Bentonite | Agents | Magnesium Stearate |
| Benzalkonium Cholide | Corn Oil | Malic Acid |
| Benzoic Acid | Cottonseed Oil | Manitol |
| Benzyl Alcohol | Dextrin | Methylcellulose |
| Butane | Dextrose | Methylparaben |
| Butylated Hydroxyanisole | Dichlorodifluoromethane | Mineral Oil |
| Burylated Hydroxyoluene | Dichlorotetrafluoroethane | Mineral Oil and Lanolin Alcohols |
| Butylparaben | Diethanolamine | Monoethanolamine |
| Precipitated Calcium Phosphate | Diethyl Phthalate | Paraffin |
| Tribasic Calcium Phosphate | Docusate Sodium | Peanut Oil |
| Calcium Stearate | Edetic Acid and Edetates | Petrolatum |
| Calcium Sulfate | Ethyl Oleate | Petrolatum and Lanolin Alcohols |
| Carbomer | Ethylcellulose | Phenylethyl Alcohol |
| Carbon Dioxide | Ethylparaben | Phenylmercuric Acetate |
| Carboxymethylcellulose Calcium | Fumaric Acid | Phenylmercuric Borate |
| Carboxymethylcellulose Sodium | Gelatin | Phenylmercuric Nitrate |
| Hydrogenated Castor Oil | Glycerin | Polacrilin Potassium |
| Cellulose Acetate Phthalate | Clyceryl Monostearate | Poloxamer |
| Microcrystalline Cellulose | Clycofurol | Polyethylene Glycol |
| Powdered Cellulose | Guar Gum | Polymethacrylates |
| Cetomacrogol | Hydrochloric Acid | Polyoxyethylene Alkyl Ethers |
| | Hydroxyethyl Cellulose | Polyoxyethylene Castor Oil Derivatives |
| | Hydroxypropyl Cellulose | Polyoxyethylene Sorbitan Fatty Acid Esters |
| | Hydroxypropyl Methylcellulose | Polyoxyethylene |
| | Hydroxypropyl Methylcellulose Phthalate | |
| | Isobutane | |
| | Isopropyl Alcohol | |

-continued

| | | |
|---|---|---|
| Emulsifying Wax | Isopropyl Myristate | Stearates |
| Cetostearyl Alcohol | Isopropyl Palmitate | Polyvinyl Alcohol |
| Cetrimide | Kaolin | Potassium Citrate |
| Cetyl Alcohol | Lactose | Potassium Sorbate |
| Cetyl Esters Wax | Lanolin | Povidone |
| Chlorhexidine | Lanolin Alcohols | Propane |
| Propylene Glycol | Tragacanth | |
| Propylene Glycol Alginate | Trichloromonofluorometh ane | |
| Propylparaben | Triethanolamine | |
| Saccharin | Pharmaceutical Waters | |
| Saccharin Sodium | Carnauba Wax | |
| Sesame Oil | Emulsifying Wax | |
| Shellac | Microcrystalline Wax | |
| Colloidal Silicon Dioxide | White Wax | |
| Sodium Alginate | Yellow Wax | |
| Sodium Ascorbate | Xylitol | |
| Sodium Benzoate | Zein | |
| Sodium Bicarbonate | Zinc Stearate | |
| Sodium Chloride | | |
| Sodium Citrate, Dihydrate and Anhydrous | | |
| Sodium Lauryl Sulfate | | |
| Sodium Metabisulfite | | |
| Sodium Starch Glycolate | | |
| Sorbic Acid | | |
| Sorbitan Esters (Sorbitan Fatty Acid Esters) | | |
| Sorbitol | | |
| Starch | | |
| Maize Starch, Sterilizable | | |
| Pregelatinized Starch | | |
| Stearic Acid | | |
| Stearyl Alcohol | | |
| Sucrose | | |
| Sugar, Compressible | | |
| Sugar, Confectioner's | | |
| Suppository Bases (Semi-Synthetic Glycerides) | | |
| Talc | | |
| Thimerosol | | |
| Titanium Dioxide | | |

A primary purpose of the subject invention is to include microcapsules in the manufacture of medicinal or pharmaceutical tablets. In one embodiment, a tablet may be made having 50% active pharmaceutical material, 45% shell material and 5% seed material. The microcapsules have a twofold job; first they strengthen the tablets and reduce the amount of breakage during the tableting or pelletizing process; and second, they control the reaction of certain substances during the dissolution process in the body. Therefore, the core, seeds and shell should be selected to provide the desired physical characteristics.

The use of the subject microcapsule in tableting provides a more efficient system, one which reduces the amount of waste during the manufacture of tablets. The subject capsule construction may provide timed release of the medicinal or pharmaceutical product protection against other chemical agents or moisture, and puts the reactants in close proximity to the active, making a more uniform and reliable tablet delivery system.

In addition, the use of seeded microcapsules increases the shelf-life of a tablet. This is because the active ingredients are physically separated from the atmosphere or other active ingredients used in the tablet by the shell.

Further, a "binary" medicine can be made in tablet form by placing a first substance in the core and a second substance that is reactive to the first substance in the seeds. The "binary" medicines are separated from each other thereby preventing any interaction between the two reactive agents until a predetermined time or event arises.

In this example, the shell is selected for its compression properties, specifically to reduce breaking during the tableting or pelletizing process. Interaction between the reactive agents is prevented until the desired moisture or acid level (i.e., inside the mouth, stomach or intestine) is reached. When the desired moisture level is achieved, the shell melts (the residue from the shell has no effect on the delivery of the active core or end-product), but the core and seeds are now exposed and can be absorbed by the body.

METHOD OF MANUFACTURING OF THE INVENTION

Figure 4:
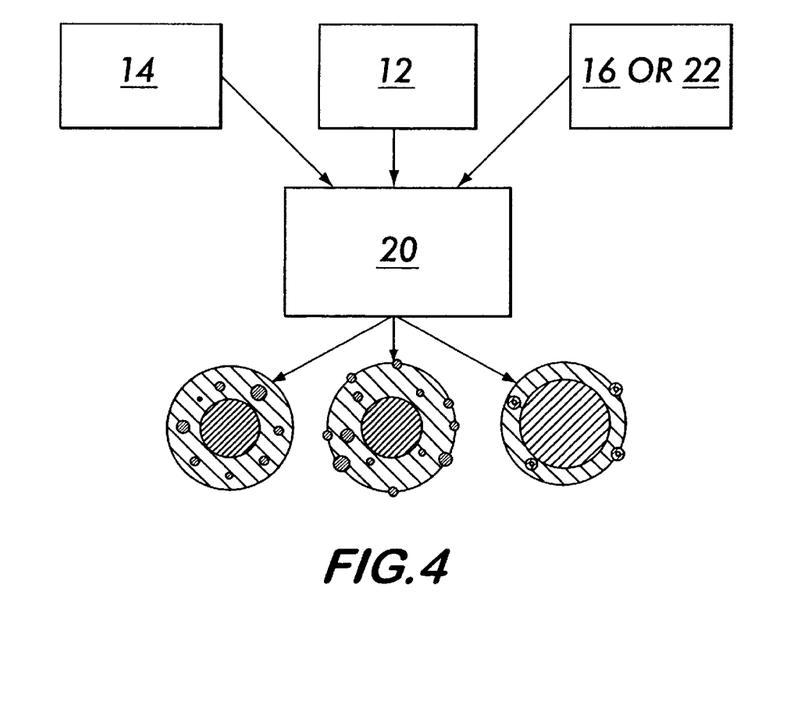
FIG. 4 is a block diagram illustration of a process for manufacturing seeded microcapsules using a granulation and mixing process.

FIG. 4 illustrates the preferred manufacturing method wherein the shell material 14 is a meltable wax or polymer, melted into a molten stage and then added to a mixer device 20.

The mixer device 20 may be a planetary mixer, a ribbon blender, a sigma mixer or such other device that rotationally blends the shell and core mixtures. The core material 12 is then added to the melted shell material while it is under agitation. The shell/core mix is maintained in the mixer under temperatures sufficient to keep the shell/core mix molten while under continued agitation. This has the effect of "wetting" the surface of the core material 12 with the shell material 14, thereby forming a layer over the core material 12. Slowly the heat is lowered—under constant agitation—until the shell layer begins to re-solidify. At this point the seed, which can be either a reactant substance, a blend of reactant substances or an encapsulated reactant 22 is added to the mixture. Continued agitation has the effect of placing the seeds 16 into the shell layer as either a embedded seed or a protruding seed as depicted in FIGS. 1, 2, and 3.

It should be noted that the size of the core depends on several factors, but primarily on the core material.

By adjusting the temperature profile of the mix blend it is possible to time the point at which the inner shell boundary 13A of FIG. 1 is formed, while still leaving enough time for the seeds 16 to be placed within the total shell thickness.

It may be necessary to add an additional quantity of molten shell after the introduction of the seeds 16, to be certain all the seeds are embedded within the shell layer as depicted in FIG. 1. By controlling the agitation speed and the amount of shell material added the seeds can be made to either be completely embedded as shown in FIG. 1 or to be protruding as shown in FIG. 2.

Figure 5:
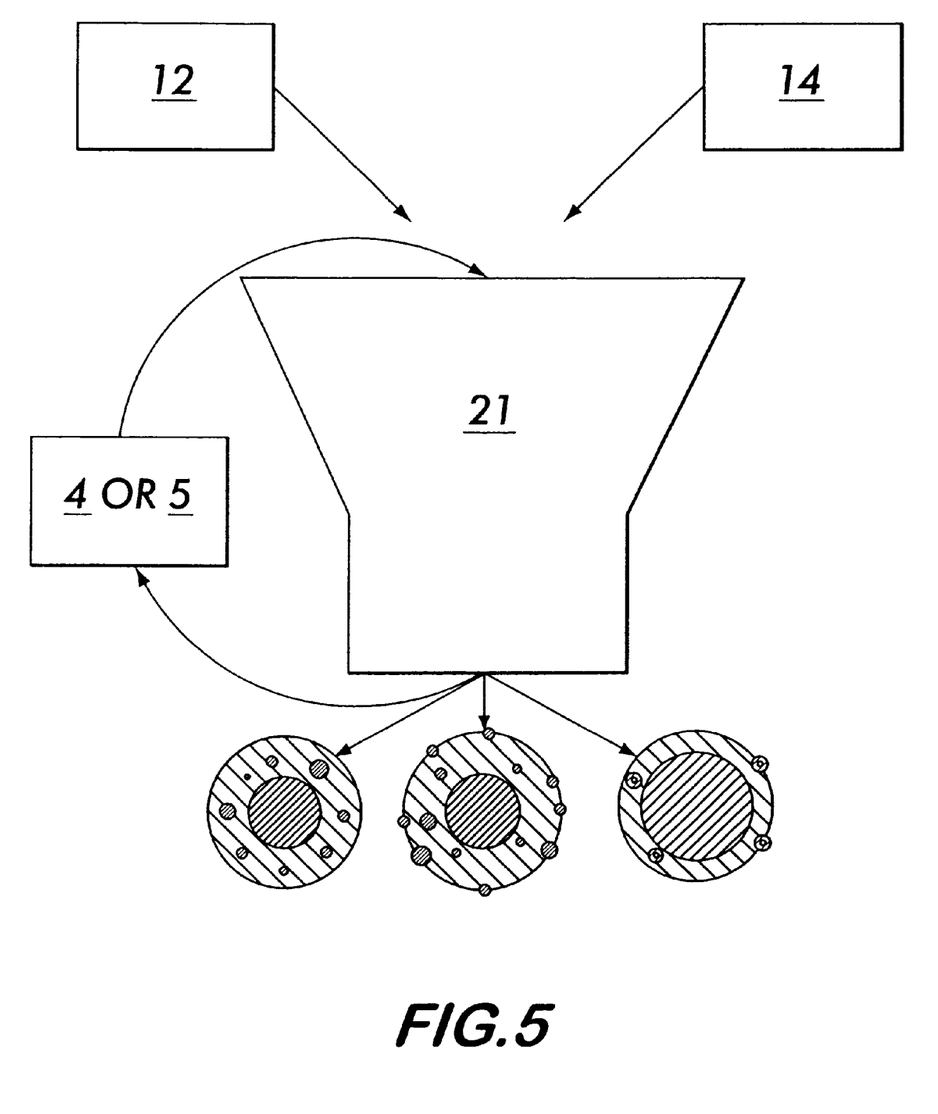
FIG. 5 is a block diagram of a manufacturing process for producing seeded microcapsules using a spray dryer coating method.
Figure 6:
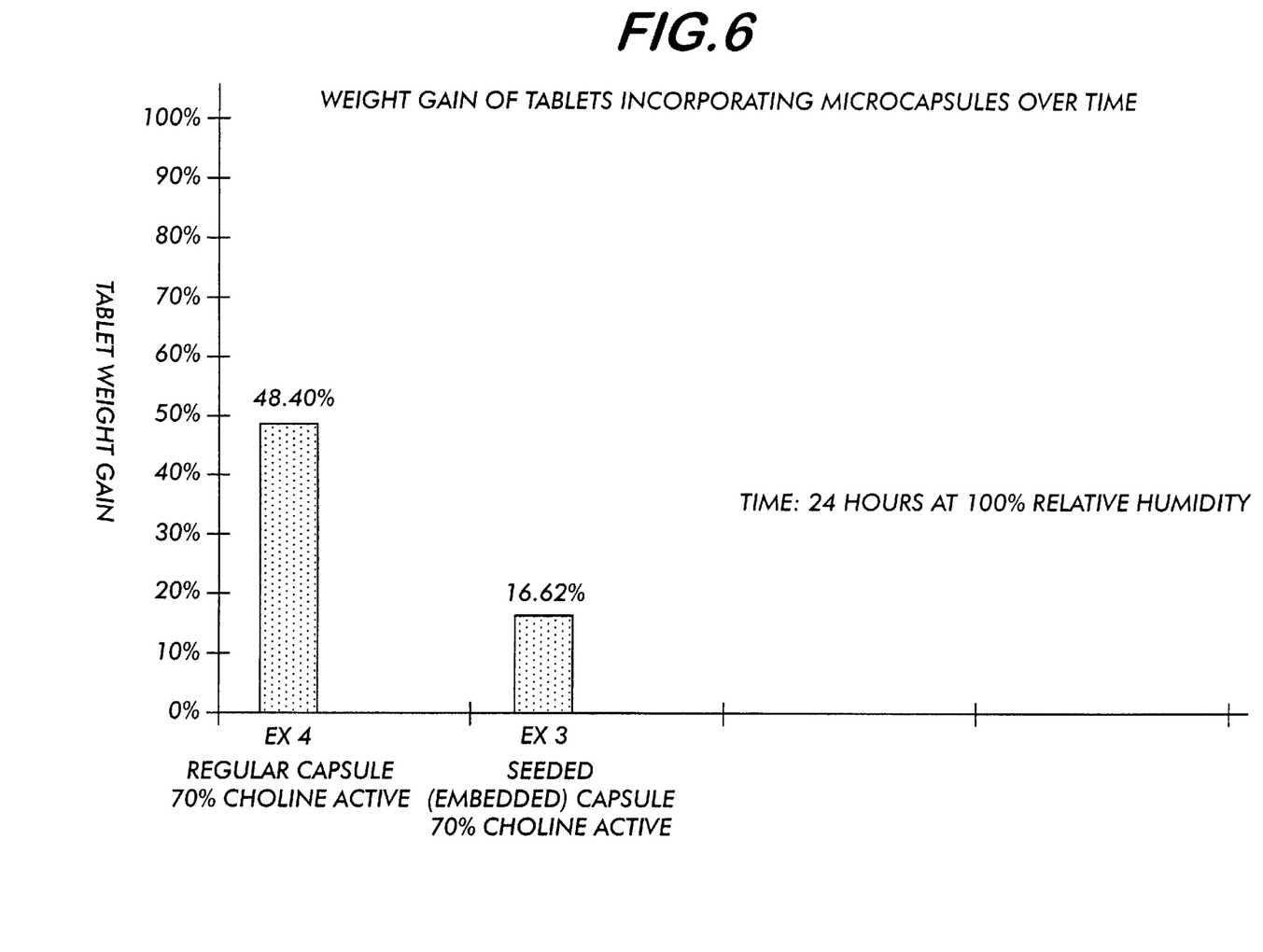
FIG. 6 is a graph of weight gain of tablets having microcapsules.

FIG. 5 shows an alternative method for manufacturing seeded microcapsules employing the use of a spray drier 21. In this embodiment the core material 12 is injected along with the shell material 14 into a spray drier 21, forming a microcapsule. The capsule is then recycled through the spray drier 21 again along with another dose of shell material, into which seed particulates, which can be either reactant substances 4 or pre-encapsulated reactants 5, have been added. On the second pass through the spray drier 21 the seeds become either embedded (as shown in FIG. 1) or protruding through the capsule shell layer (as shown in FIG. 2). This may be done by adjusting the thickness of the shell layer. The finished capsule product 1 is formed at the conclusion of the second pass through the spray drier.

While a spray drier 21 is depicted in the above embodiment, any other mechanical means of effecting microcapsules may be utilized including but not limited to fluid bed driers, worster fluid bed, extrusion devices, centrifugal extrusion devices or the M-CAP systems described in U.S. Pat. Nos. 4,978,483 and 5,271,881.

EXPERIMENTAL EXAMPLES

Experiment 1: Seeded Vitamin-C Microcapsules Using Protruding Seed Construction

A 1,000 gram vitamin-C seeded capsule is made by mixing 700 grams of ascorbic acid with 250 grams of molten cottonseed vegetable wax in a hobart mixer. The hobart mixer is agitated for 30 minutes while maintaining a temperature greater than the melt point of the cottonseed wax. In the preferred embodiment, the temperature is 155° F. (i.e., 20° F. above the melt point of the cottonseed wax). The heat is then terminated. Agitation is maintained while the mixture cools to approximately 135° F. (i.e., the melt point of the cottonseed wax), at which point 50 grams of micronized microcrystalline cellulose is added to the mixture. The mixing action is continued until the mixture reaches ambient temperature, at which point the vegetable wax has solidified into a hard coating about the ascorbic acid, forming a shell layer into which the microcrystalline cellulose has become partially embedded. This process forms a protruding capsule construction similar to the one depicted in FIG. 2. These capsules contain 70% active core material, 25% shell material and 5% seed.

EX#1 is the designation for capsules made under this technique. The protruded shell construction of Sample EX-1 provides for a slow interaction release of the Vitamin C until the shell is totally dissolved away. After the shell is completely dissolved (i.e., preferably when in the small intestine) there is a fast release of the Vitamin C at this point.

Experiment 2: Seeded Vitamin-C Microcapsules Using Embedded Seed Construction

A 1,000 gram vitamin-C seeded capsule is made by mixing 700 grams of ascorbic acid with 125 grams of molten cottonseed vegetable wax in a hobart mixer. The hobart mixer is agitated for 30 minutes while maintaining a temperature greater than the melt point of the cottonseed wax. Again, in the preferred embodiment, the temperature is approximately 155° F. (i.e., about 20° F. above the melt point of the cottonseed wax). The heat is then terminated. When the mixture has cooled to approximately 135° F. and the mixtures continues to be agitated, 50 grams of micronized microcrystalline cellulose is added to the mixture. The mixing action is continued until the mixture reaches ambient temperature, at which point the vegetable wax has solidified into a hard coating about the ascorbic acid, forming a shell layer into which the microcrystalline cellulose has become embedded, forming a protruding capsule construction. These protruding capsules are then removed from the mixer and placed in a second mixer to which another 125 grams of molten cottonseed vegetable wax has been added. The heat is removed and the mixture continuously agitated until this second capsule mix is cooled to ambient temperature. The second application of shell material forms a complete enclosure about the seeded microcrystalline cellulose resulting in a capsule construction similar to FIG. 1 with fully embedded seeds. These capsules contain 70% active core material, 25% shell material and 5% seed.

EX#2 is the designation for capsules made under this technique. The sample of EX-2 uses the embedded capsule construction of FIG. 1 and delays interaction until the shell is totally dissolved.

Experiment 3: Seeded Choline Microcapsules Using Embedded Seed Construction

A 1,000 gram seeded capsule of choline is made by mixing 700 grams of Choline chloride with 125 grams of molten cottonseed vegetable wax in a hobart mixer. The hobart mixer is agitated for approximately thirty minutes while maintaining a temperature greater than the melt point of the cottonseed wax. In the preferred embodiment, the mixture is heated to approximately 155° F. While continuing to agitate the mixture, the heat is then terminated and the mixture is allowed to cool to about 135° F.; at this time, 50 grams of micronized microcrystalline cellulose is then added to the mixture. The mixing action is continued until ambient temperature is reached, at which point the vegetable wax has solidified into a hard coating about the Choline particle, forming a shell layer into which the microcrystalline cellulose has become embedded, forming a protruding capsule construction. The capsules are then removed from the first mixer and added to a second mixer which is agitating another 125 grams of molten cottonseed wax. The heat is removed and the mixture continuously agitated until the new capsule mix is cooled to ambient temperature. The second application of shell material forms a complete enclosure about the first shell layer resulting in a capsule construction similar to FIG. 1 with fully embedded seeds. These capsules contain 70% active core material, 25% shell material and 5% seed, and are referred to as EX-3.

PROCEDURE FOR MANUFACTURE OF MICROCAPSULES

For comparison purposes the process of manufacturing encapsulated ascorbic acid will be compared to the manufacture of encapsulated Choline, without the use of seeded shell constructions. The samples are made according to the same standard procedure minus the addition of the seeded particulates to the shell. The procedure is as follows:

1,000 grams of a capsule product, containing either ascorbic acid or Choline respectively, is made by mixing 700 grams of the active with 300 grams of molten cottonseed vegetable wax in a hobart mixer. The hobart mixer is agitated for thirty minutes while maintaining a temperature greater than the melt point of the cottonseed wax (i.e., preferably about 155° F.). The heat is then terminated and allowed to air cool until ambient while maintaining agitation, at which point the vegetable wax has solidified into a hard coating about the active core particle, forming a shell layer. The encapsulated particle contains 70% active and 30% shell. The sample of encapsulated ascorbic acid made according to this procedure is labeled EX-4, while the sample of encapsulated Choline is labeled EX-5.

TABLET FORMULATION

The above samples are compared to control sample versions after a tableting operation employing a standard tableting formulation with direct compression at a standard pressure setting of 2,000 lbs.

| ENCAPSULATED INGREDIENT | 420 mg. | 63.8% |
| --- | --- | --- |
| (active ingredient @ 70% core) | (294) | (44.7%) |
| Dicalcium Phosphate | 230 mg. | 34.9% |
| Magnesium Stearate | 6 mg. | 0.91% |
| Aerosol R972 | 2 mg. | 0.30% |
| TOTAL | 658 mg. | 100% |

| TABLETING CONDITIONS: | |
| --- | --- |
| Room Humidity | 60% Relative Humidity |
| Tool Size | 1/2 inch |
| Table Punch Pressure | 2,000 lbs. |
| Tableting Method | Direct Compression |

LEGEND

The rate of dissolution can be adjusted through the use of a seeded microcapsule, offering a controlled delivery effect.

Referring now to FIGS. 6, 7, 7A, 7B and 7C, the manufacturing of the tablet will be discussed.

Figure 7A:
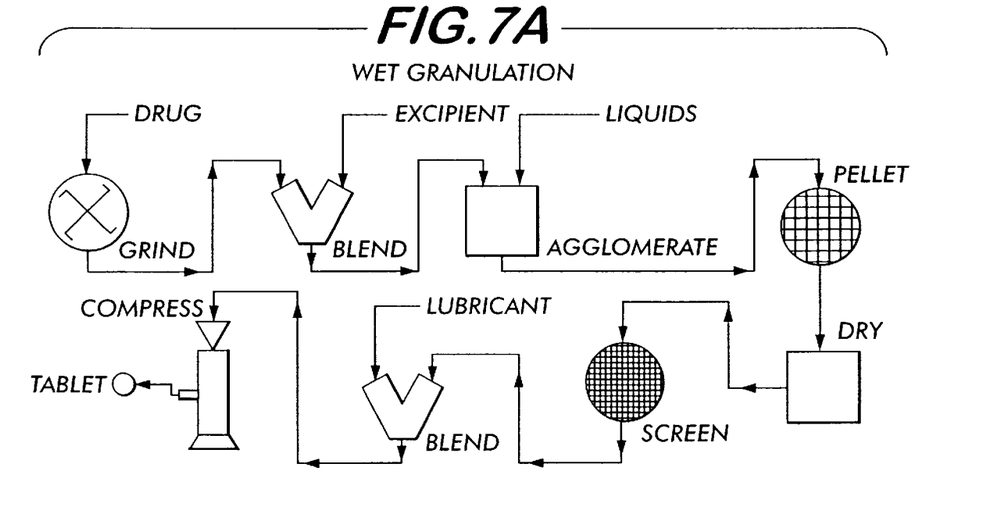
FIG. 7A is a block diagram of a manufacturing process for tablets using wet granulation.
Figure 7B:
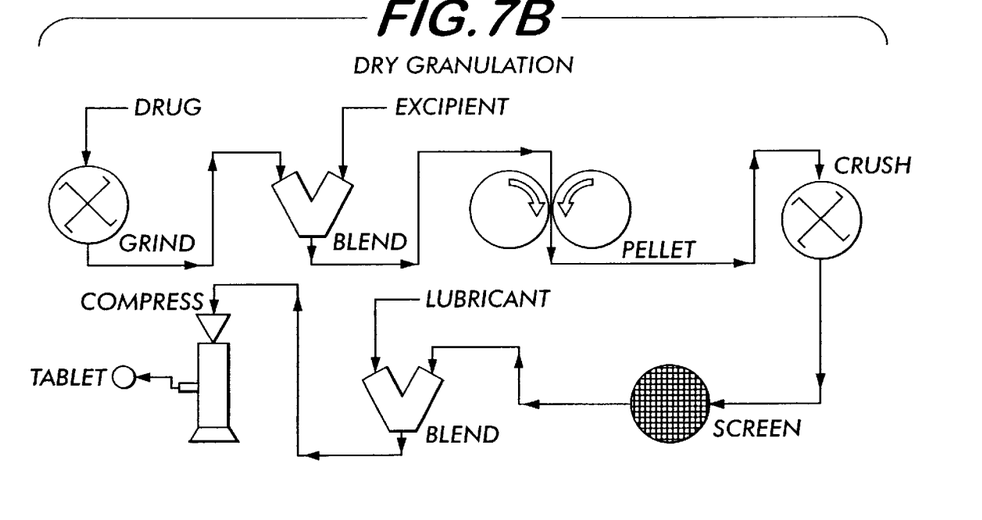
FIG. 7B is a block diagram of a manufacturing process for tablets using dry granulation.
Figure 7C:
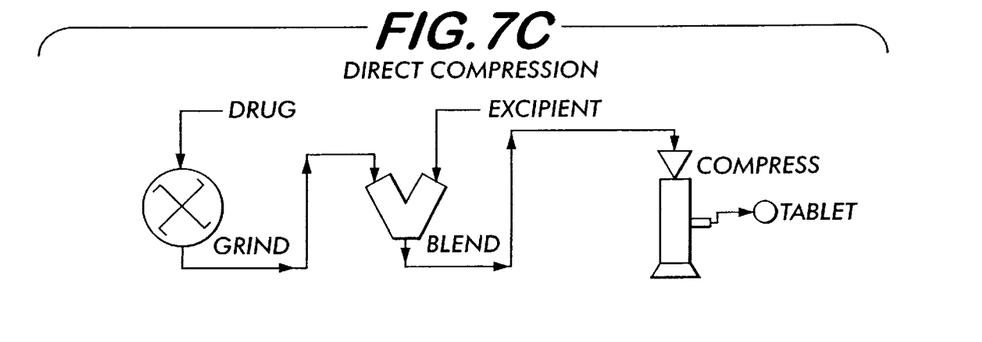
FIG. 7C is a block diagram of a manufacturing process for tablets using direct compression.

As shown in FIG. 8, in which the direct compression method of making a tablet is illustrated, the drug in its microencapsulated state is combined with excipients and blended together. The blend is then measured and/or weighed and separated into individual portions. These individual portions are then compressed and a tablet is formed.

In the manufacture of acetaminophen tablets, microapsules are made as described previously in which the acetaminophen often forms the core, sodium bicarbonate forms the seed and wax forms the shell. The excipient will form the shell of the microcapsule. The sodium bicarbonate seeds act to resist tableting pressures but will virtually explode upon contact with gastric fluid in the stomach which is acidic. This explosion will force a fast release of the active ingredient and will tend to provide fast relief for the user's headache.

Seeded microcapsules can also be used to control other properties. For example, choline is a highly hygroscopic material. If exposed to air, choline will draw moisture from the atmosphere and become very soft. Choline in a seeded microcapsule greatly reduces the amount of moisture choline can draw from the air.

While anyone skilled in the art of encapsulation may develop alternative compositions to this invention after a reading of this specification, such developments are deemed to fall within the scope of this invention in that reactant compounds used in close proximity to an encapsulated active substance can provide a controlled release in tablets. Where the term microcapsule is used it would be obvious to anyone skilled in the art that the general term capsule or microparticle or microgranule may also be employed.

Although the present invention has been described with reference to the particular embodiments herein set forth, it is understood that the present disclosure has been made only by way of example and that numerous changes in details of construction may be resorted to without departing from the spirit and scope of the invention. Thus, the scope of the invention should not be limited by the foregoing specifications, but rather only by the scope of the claims appended hereto.

What is claimed is:

1. A microcapsule for use in a medicinal tablet, said microcapsule including a core surrounded by a shell, the microcapsule comprising:

(a) a first substance that forms the core;

(b) a second substance that forms the shell; and (c) a third substance in the form of a plurality of seeds dispersed throughout said shell wherein at least a portion of said plurality of seeds are themselves encapsulated.

2. The microcapsule of claim 1 wherein said plurality of seeds is completely embedded in said shell.

3. The microcapsule of claim 1 wherein at least a portion of said plurality of seeds protrude through the outer surface of said shell.

4. The microcapsule of claim 1 wherein all of said plurality of seeds protrude through the surface of said shell.

5. The Microcapsule of claim 1 wherein the seeds of the capsule are selected from the group consisting of

| | | |
|---|---|---|
| Acacia, | Carbomer, | Chlorobutanol, |
| Alcohol, | Carbon Dioxide, | Cholesterol, |
| Alginic Acid, | Carboxymethylcellulose | Citric Acid, |
| Ascorbic Acid, | Calcium, | Pharmaceutical Coloring |
| Bentonite, | Carboxymethylcellulose | Agents, |
| Benzalkonium Cholide, | Sodium, | Corn Oil, |
| Benzoic Acid, | Hydrogenated Castor | Cottonseed Oil, |
| Benzyl Alcohol, | Oil, | Dextrin, |
| Butane, | Cellulose Acetate | Dextrose, |
| Butylated | Phthalate, | Dichlorodifluoromethane, |
| Hydroxyanisole, | Microcrystalline | Dichlorotetrafluoroethane, |
| Burylated | Cellulose, | Diethanololamine, |
| Hydroxyoluene, | Powdered Cellulose, | Diethyl Phthalate, |
| Butylparaben, | Cetomacrogol | Docusate Sodium, |
| Precipitated Calcium | Emulsifying Wax, | Edetic Acid and Edetates, |
| Phosphate, | Cetostearyl Alcohol, | Ethyl Oleate, |
| Tribasic Calcium | Cetrimide, | Ethylcellulose, |
| Phosphate, | Cetyl Alcohol, | Ethylparaben, |
| Calcium Stearate, | Cetyl Esters Wax, | Fumaric Acid, |
| Calcium Sulfate, | Chlorhexidine, | Gelatin, |
| Glycerin, | Polyethylene Glycol, | Sterilizable, |
| Clyceryl Monostearate, | Polymethacrylates, | Pregelatinized Starch, |
| Clycofurol, | Polyoxyethylene Alkyl | Stearic Acid, |
| Guar Gum, | Ethers, | Stearyl Alcohol, |
| Hydrochloric Acid, | Polyoxyethylene | Sucrose, |
| Hydroxyethyl Cellulose, | Sorbitan Fatty | Sugar, Compressible, |
| Hydroxypropyl Cellulose, | Acid Esters, | Sugar, Confectioner's, |
| Hydroxypropyl | Polyoxyethylene | Suppository Bases, |
| Methylcellulose, | Stearates, | Talc, |
| Hydroxypropyl | Polyvinyl Alcohol, | Thimerosol, |
| Methylcellulose | Potassium Citrate, | Titanium Dioxide, |
| Phthalate, | Potassium Sorbate, | Tragacanth, |
| Isobutane, | Povidone, | Trichloromonofluoromethane, |
| Isopropyl Alcohol, | Propane, | Triethanolamine, |
| Isopropyl Myristate, | Propylene Glycol, | Pharmaceutical Waters, |
| Isopropyl Palmitate, | Propylene Glycol | Carnauba Wax, |
| Kaolin, | Alginate, | Emulsifying Wax, |
| Lactose, | Propylparaben, | Microcrystalline Wax, |
| Lanolin, | Saccharin, | White Wax, |
| Lanolin Alcohols, | Saccharin Sodium, | Yellow Wax, |
| Lecithin, | Sesame Oil, | Xylitol, |
| Magnesium Aluminium | Shellac, | Zein, and |
| Silcate, | Colloidal Silicon Dioxide, | Zinc Stearate. |
| Magnesium Stearate, | Sodium Ascorbate, | |
| Malic Acid, | Sodium Benzoate, | |
| Manitol, | Sodium Bicarbonate, | |
| Methylcellulose, | Sodium Chloride, | |
| Methylparaben, | Sodium Citrate, | |
| Mineral Oil, | Dihydrate and | |
| Mineral Oil and Lanolin | Anhydrous, | |
| Alcohols, | Sodium Lauryl Sulfate, | |
| Monoethanolamine, | Sodium Metabisulfite, | |
| Paraffin, | Sodium Starch, | |
| Peanut Oil, | Glycolate, | |
| Petrolatum, | Sorbic Acid, | |
| Petrolatum and Lanolin | Sorbitan Esters, | |
| Alcohols, | Sorbitol, | |
| Phenylethyl Alcohol, | Starch, | |
| Phenylmercuric Acetate, | Maize Starch, | |
| Phenylmercuric Borate, | | |
| Phenylmercuric Nitrate, | | |
| Polacrilin Potassium, | | |
| Poloxamer, | | |

6. The microcapsule of claim 1 wherein said third substance is chosen to react with said first substance when said shell deteriorates.

7. The microcapsule of claim 1 wherein said first substance is selected from the group consisting of aspirin, acetaminophen, ascorbic acid, citric acid, monocalcium phosphate, sodium acid pyrophosphate, a mineral supplement, a vitamin, choline, and ibuprofen.

8. A microcapsule having a multiple-stage release, comprising:
(a) a first substance for forming a core;
(b) a second substance for use as a shell;
(c) a third substance in the form of a first plurality of seeds captured by said shell; and
(d) a fourth substance in the form of a second plurality of seeds captured by said shell wherein the first and second plurality of seeds are released at the occurrence of a first triggering event and the core is released at the occurrence of a second triggering event.

9. The microcapsule of claim 8 wherein the first plurality of seeds is comprised of a base material, the second plurality of seeds is comprised of an acid, and the core is comprised of a pharmaceutical agent.

10. The microcapsule of claim 9 wherein said core is aspirin.

11. The microcapsule of claim 1 wherein said shell is chosen to deteriorate at a pre-determined temperature.

12. The microcapsule of claim 9 wherein said core is comprised of ascorbic acid.

13. The microcapsule of claim 1 wherein said first substance is a liquid.

14. The microcapsule of claim 1 wherein said first substance is a solid.

* * * * *